United States Patent [19]

Spevak et al.

[11] 4,337,779
[45] Jul. 6, 1982

[54] PHYSIOLOGICAL EVENT DETECTOR

[75] Inventors: Richard P. Spevak, Moundsview; Lynn D. Hansen, Fridley, both of Minn.

[73] Assignee: Medtronic, Inc., Minneapolis, Minn.

[21] Appl. No.: 176,900

[22] Filed: Aug. 11, 1980

[51] Int. Cl.³ .............................................. A61B 5/02
[52] U.S. Cl. ................................................. 128/691
[58] Field of Search ............. 128/419 D, 702, 703, 128/705, 708, 696, 693, 694, 687, 688

[56] References Cited

U.S. PATENT DOCUMENTS 3,144,019  8/1964  Haber .................................. 128/705
3,939,824  2/1976  Arneson et al. ..................... 128/708
4,191,195  3/1980  Miller ................................. 128/696

Primary Examiner—William E. Kamm
Attorney, Agent, or Firm—Robert C. Beck; John L. Rooney; Joseph F. Breimayer

[57] ABSTRACT

A physiological event detector including apparatus for receiving and detecting an electrical signal corresponding to a physiological event. The apparatus produces a logic level output when the input signal meets both passband energy criteria and time duration criteria. The structure of the invention includes a filter for selecting the passband criteria and digital timing circuitry for determining how long the passband signal exceeds a minimum energy threshold.

3 Claims, 1 Drawing Figure

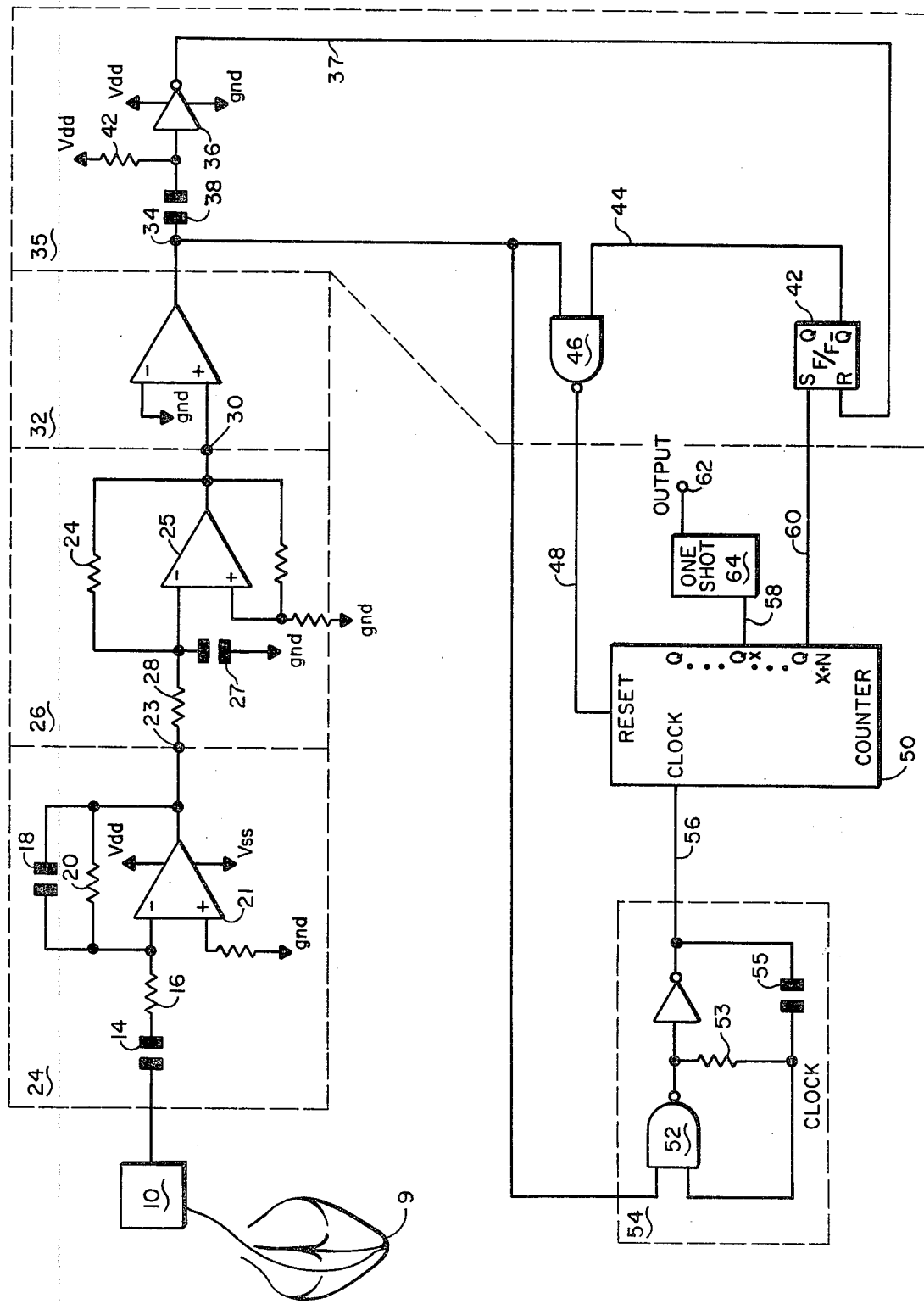

PHYSIOLOGICAL EVENT DETECTOR

BACKGROUND OF THE INVENTION

1. Field of the Invention

This invention relates to apparatus for detecting the occurrence of a physiological event based upon an analysis of an electrical waveform associated with the event. The detector may be used as a sense amplifier for use in a pacemaker or it may be used with a cardiac impedance plethysmograph, for use in an automatic implantable defibrillator.

2. Description of the Prior Art

Both demand pacemakers and automatic implantable defibrillators (AID) require circuitry responsive to cardiac activity. In the case of the demand pacemaker, the detection of spontaneous cardiac electrical activity inhibits or prevents the delivery of a stimulating pulse to the heart. In the case of the implantable automatic defibrillator the detection of abnormal cardiac activity is sensed by the AID which delivers a high voltage cardioverting stimulus to the heart. This cardioverting stimulus may injure the patient if it is delivered when it is not needed since it may cause life-threatening arrhythmias.

Consequently, much work has been devoted to developing detectors which reliably sense cardiac activity. In the case of the AID, this is normally accomplished by sensing the mechanical pumping action of the heart as well as the electrical activity generated by the heart. When both the electrical activity and mechanical activity of the heat fail to meet established criteria, the cardioverting output stimulus is produced. Early methods of detecting the mechanical activity of the heart include pressure transducers as taught by U.S. Pat. Nos. 3,614,955 and 3,614,954 to Mirowski et al. These pressure transducers proved unreliable in practice and were replaced by elastomeric transducers as taught by U.S. Pat. No. 3,815,611 to Denniston. Although this form of sensor proved more reliable than the pressure transducer, the difficulty in accurately locating such an elastomeric transducer catheter prevented its widespread adoption.

A further means for detecting cardiac activity comprises a blood impedance plethysmograph which measures the impedance between two spaced electrodes placed on a catheter located within a ventricle of the heart. The volume of blood within the ventricle varies over time as the heart pumps and alters the impedance of the chamber as measured between the spaced electrodes. During normal heart activity the impedance transducer output varies relatively slowly providing a low slew rate signal, which must be detected in the presence of high frequency noise. This problem has not been overcome by prior art detectors such as that taught by U.S. Pat. No. 3,805,795 to Denniston, which do not measure the duration of the impedance signal.

SUMMARY OF THE INVENTION

In contrast to the prior art the physiological event detector of the present invention takes into account the duration of the physiological event which is to be sensed. In operation, the physiologic signal is passed through a frequency selective network which selectively attenuates signal components outside of a defined passband. When the energy within this passband exceeds a preset minimum level, a time-measuring circuit is activated which determines the length of time during which the passband energy of the input signal exceeds this predetermined minimum energy level. In this context, the term energy refers to the distribution of frequency components of the waveform in the frequency domain. This results in a measurement of the duration of the impedance signal which is a reliable indicator that the input waveform from the plethysmograph has resulted from cardiac pumping activity. The structure which accomplishes this function includes a filter and switched oscillator section which receives the electrical signal and which produces a logic level output when the minimum energy criteria is met. This logic level signal gates clock pulses to a digital counter which counts the number of clock pulses from a clock corresponding to the duration of the physiological signal. The detector output may be taken from a specific count output of the counter, thus establishing a minimum time duration signal which will be detected or identified as a physiological event.

The many advantages and novel features of the present invention will become apparent from the following detailed description of the invention when considered in conjunction with the accompanying drawings.

BRIEF DESCRIPTION OF THE DRAWING

The FIGURE is a schematic diagram of the physiological event detector of the present invention.

DESCRIPTION OF THE PREFERRED EMBODIMENT

As previously described, the detector of the present invention accepts an electrical signal from an impedance plethysmograph 10 and produces a detector output at terminal 62 if the waveform from the phethysmograph meets passband energy criteria and waveform duration criteria.

The analog portion of the detector, which includes filter 24, swtich oscillator 26 and Buffer 32, perform the passband energy detection function.

The digital portion of the circuitry, which includes reset logic 35, clock 54 and counter 50, performs the waveform duration measurement function.

In operation, the analog portion of the circuitry produces a voltage level at node 34 at the output of Buffer 32 which indicates that the input waveform from the plethysmograph 10 has met the passband energy requirement. This voltage level initiates the operation of digital circuitry which produces a single logic level pulse at terminal 62 if the input waveform also satisfies the duration criteria set by the digital circuitry.

ANALOG SECTION

The impedance plethysmograph 10 includes circuitry which measures the impedance of the ventricle of the heart 9 and amplifies and buffers the signal to a level suitable for use by the detector system of the present invention. This signal is coupled to the filter 24 of the detector. In the preferred embodiment the filter has passband characteristics defined by −3dB points of 0.5 Hz and 20 Hz. and has a nominal gain of 1. These passband and gain characteristics of operational amplifier 21 are set by an input capacitor 14 and resistor 16 coupled with feedback capacitor 18 and resistor 20. The output of filter 24 at node 23 has a value which corresponds to the input signal from the plethysmograph 10. The passband filtered signal is coupled to the switched oscillator 26.

The switched oscillator comprises an operational amplifier 25 as the active element and a number of passive components. This switched oscillator will produce a squarewave of 1 kHz at node 30 if the applied input from node 23 is below a minimum threshold. The switched oscillator will produce a DC voltage level at node 30 if the input signal at node 23 exceeds this minimum threshold. The frequency of the squarewave output is determined by the value of the feedback resistance 29 and input capacitor 27. The threshold of the device is set by the ratio of feedback resistor 29 and input resistor 28. The additional resistors shown in the diagram limit current draw of the operational amplifier and form of the bias network for the operational amplifier 25.

The signal available at node 30 is coupled to Buffer 32 which increases or improves the rise and fall times for the signals for the switched oscillator and also provide sufficient current to drive the digital portion of the circuit.

In summary, the analog portion of the circuit including filter 24, switched oscillator 26 and Buffer 32 cooperate to produce a logic level signal at node 34 which indicates the input signal plethysmograph 10 has met bandpass criteria set by filter 24 and energy threshold criteria determined by switched oscillator 26.

DIGITAL SYSTEM

The digital system of the present invention measures the time duration of the input waveform from the plethysmograph 10. This system includes a clock 54 which provides clock pulses to a counter 50. The clock and counter are started when the input waveform meets the criteria set by the analog circuitry. If the input signal exceeds the energy criteria of the analog circuitry for a time period long enough to reach a specified count of the counter 50 then an output pulse is produced by one-shot 64 and is available to the pacemaker or defibrillator through output terminal 62. Additional reset logic is provided to insure that the counter is reset to 0 at the trailing edge of the physiological signal and also to insure that unusally long waveforms are not detected twice i.e. a long-duration pulse will not produce multiple outputs at terminal 62.

Turning once again to the FIGURE, a logic 1 voltage level at node 34 indicates that the input waveform has met the bandpass and energy threshold set by the analog circuitry. The negative going transition at node 34 triggers the one-shot formed by NOT gate 36 and resistor 40 and capacitor 38. The output pulse on lead 37 from the one-shot is used to reset flip flop 42. This produces a logic 1 on the NOTQ terminal of the flip flop 42. This signal is communicated via lead 44 to NAND gate 46. The other lead of NAND gate 46 is also coupled to node 34 and as a consequnce the output of the NAND gate 46 will go to a logic 1. This signal on lead 48 is used as a reset pulse for counter 50 and remains reset until the next positive transition of node 34. As a consequence, these logic element cooperate to reset counter 50 to "0" at the end of the physiological waveform.

Also, the logic 1 voltage level of node 34 is communicated to NAND gate 52 which turns on clock 54. The clock delivers clock pulses via lead 56 to the clock input of counter 50. The frequency of these clock pulses is determined by the R-C product of resistor 53 and capacitor 55. In the preferred embodiment shown, the frequency of clock 54 is 100 Hz. In operation, if the input waveform is sufficient to enable clock 54 for a time period determined by a selected counter output 58 then the clock transition on counter output 58 will initiate a pulse from one-shot 64 indicating that the physiological waveform has satisfied the minimum time duration set by the clock 54 and counter 50.

It is important to note however, that the counter is not reset to 0 or disabled once the physiological event has been detected. As long as the clock is enabled, counter 50 will continue to count until it reaches a count indicated by output 60 which sets the Q output of flip flop 42 to "1", and the NOTQ output of flip flop 42 to 0 thus applying a logic 1 via lead 48 to reset input of counter 50.

A time interval extending from the count corresponding to terminal 58 to the count associated with terminal 60 may be considered a blanking interval during which the system will be refractory to a new input.

PARAMETERS

The foregoing has been a description of a detector which requires that the input signal meet both passband energy criteria as well as waveform duartion criteria before the detection criteria is met. In the form described the detector is suitable for use with a plethysmograph which measures the impedance of a ventricle of the heart. The passband criteria of filter 24, the oscillator frequency of switched oscillator 26 and the clock frequency of clock 54 as well as the counter output of counter 50 have been optimized for this task. However, it should be clear that these parameters may be altered to permit the optimized detection of other physiological waveforms including intracardiac R-waves. It is important to note that the resolution of this system depends on the clock frequency and that by selecting an appropriate clock frequency one may exclude high frequency noise which meets the passband energy requirements but which does not persist long enough to permit counter 50 to reach the count corresponding with terminal 58.

The choice of component values for the passband filter will determine how much high frequency noise will be attenuated within the physiological event passband. High frequency noise of sufficient amplitude may contain sufficient summated energy components within the allowed passband to cause the switched oscillator output 34 to go to logic 1 and thus enable the clock 54 and the counter 50.

The inherent nature of the high frequency noise signal is such that it will cause the switched oscillator to revert back to its oscillatory state within a short time—because it will pass below the minimum level criteria. When this occurs the counter will be reset. Proper selection of clock frequency and count value will assure that the noise signal is not detected as a physiological event. The clock frequency will determine the resolution of the detection algorithm and the count value will determine the duration of the measured parameter.

If the noise signal is summated with a physiological event and the filtered signal is of sufficient energy to maintain the switched oscillator in the high level 1 state then the noise level will not interfere with the detection of the physiological event.

Obviously, there are numerous other modifications which may be introduced to optimize this detector for different applications. Therefore, it should be understood that within the scope of the appended claims the invention may be practiced otherwise than as described in the specification.

What is claimed is:

1. An improved physiologic waveform discriminator for detecting the mechanical pumping action of the heart based upon an impedance plethysmograph signal produced by an impedance plethysmograph coupled to the heart for producing a time varying electrical plethysmograph signal determined by the instantaneous volume of heart, wherein said improvement comprises;
   frequency selective means for amplifying passband components of said plethysmograph signal for producing a passband signal;
   time measuring circuitry activated when said passband components of said plethysmograph signal exceed a predetermined level for measuring the time period duration that said passband components of said plethysmograph signal exceed said predetermined level; and,
   output circuitry for producing an output detection signal when said time period duration exceeds a preset minimum duration.

2. The discriminator of claim 1 wherein said frequency selective means includes a passband amplifier of nominal unity gain for attenuating signal components below approximately 0.5 Hertz and above approximately 20 Hertz.

3. The discriminator of claim 2 wherein said time measuring circuitry includes:
   A switched oscillator coupled to said frequency selective means for producing a squarewave output if said passband signal is below a minimum threshold, and for producing a continuous logic level output if said passband signal exceeds said minimum threshold;
   a clock means activated by said logic level signal for supplying clock pulses to counter means;
   said counter means for accumulating clock pulses for the period of time that said passband signals exceeds said minimum threshold; and,
   output circuitry means coupled to said counter means for producing an output detection signal when said counter accumulates a preset number of clock counts indicating that said impedance plethysmograph signal has exceeded a predetermined time period.

* * * * *